United States Patent
Gouveia Alves et al.

(10) Patent No.: US 11,523,607 B2
(45) Date of Patent: Dec. 13, 2022

(54) SPERM STORAGE MEDIA COMPRISING MHY 1485 FOR ENHANCING SPERM QUALITY AND FUNCTION

(71) Applicant: UNIVERSIDADE DO PORTO, Oporto (PT)

(72) Inventors: Marco Aurélio Gouveia Alves, Oporto (PT); Carlos Pedro Fontes Oliveira, Oporto (PT); Mário Manuel Da Silva Leite De Sousa, Oporto (PT); Tito Miguel Boléo Teles De Jesus, Oporto (PT); Susana Paula Pinto De Almeida, Oporto (PT)

(73) Assignee: UNIVERSIDADE DO PORTO, Oporto (PT)

( * ) Notice: Subject to any disclaimer, the term of this patent is extended or adjusted under 35 U.S.C. 154(b) by 231 days.

(21) Appl. No.: 16/636,057

(22) PCT Filed: Jul. 31, 2018

(86) PCT No.: PCT/IB2018/055715
§ 371 (c)(1),
(2) Date: Feb. 3, 2020

(87) PCT Pub. No.: WO2019/025961
PCT Pub. Date: Feb. 7, 2019

(65) Prior Publication Data
US 2020/0205400 A1 Jul. 2, 2020

(30) Foreign Application Priority Data
Aug. 2, 2017 (PT) .......................................... 110231

(51) Int. Cl.
*A01N 1/02* (2006.01)
*A61K 35/48* (2015.01)

(52) U.S. Cl.
CPC ............ *A01N 1/0226* (2013.01); *A61K 35/48* (2013.01)

(58) Field of Classification Search
None
See application file for complete search history.

(56) References Cited

U.S. PATENT DOCUMENTS

2017/0290890 A1* 10/2017 Cheng .................... A61K 38/24

FOREIGN PATENT DOCUMENTS

WO    0107021 A2    2/2001
WO    2016040493 A1    3/2016

OTHER PUBLICATIONS

Caravalho B. et al. Activation of mTOR Pathway During Short Term Preservation Increases Spermatozoa Glycolytic Activity European J of Clinical Investigation 50(Suppl 1)29-30, Sep. 2020. (Year: 2020).*
Joana Vieira Silva, M.Sc. et al. "Profiling signaling proteins in human spermatozoa: biomarker identification for sperm quality evaluation" Fertility and Sterility® vol. 104, No. 4, Oct. 2015, American Society for Reproductive Medicine, Published by Elsevier Inc.
Elena Lorenzi et al. "Infertility risk and teratogenicity of molecularly targeted anticancer therapy: A challenging issue" Critical Reviews in Oncology/Hematology, vol. 107, Nov. 2016, pp. 1-13.
I. M. Aparicio, J. Espino, I. Bejarano, A. Gallardo-Soler, M. L. Campo and G. M. Salido (2016), "Autophagy-related proteins are functionally active in human spermatozoa and may be involved in the regulation of cell survival and motility." Scientific Reports 6: 33647.
J. A. Pariente, F. J. Pena & J. A. Tapial Elder, K. and B. Dale (2010). In-vitro fertilization, Cambridge University Press.
Jackson, R. E., C. L. Bormann, P. A. Hassun, A. M. Rocha, E. L. Motta, P. C. Serafini and G. D. Smith (2010). "Effects of semen storage and separation techniques on sperm DNA fragmentation." Fertility and sterility 94(7): 2626-2630.
Jesus, T. T., P. F. Oliveira, J. Silva, A. Barros, R. Ferreira, M. Sousa, C. Y. Cheng, B. M. Silva, and M. G. Alves (2016). "Mammalian target of rapamycin controls glucose consumption and redox balance in human Sertoli cells." Fertil. Steril. 150(3): 825-833.e823.
Oliveira, P. F., C. Cheng and M. G. Alves (2017). "Emerging Role for Mammalian Target of Rapamycin in Male Fertility." Trends in Endocrinology & Metabolism: DOI: 10.1016/j.tem.2016.1012. 1004.
Sato, M. and A. Ishikawa (2004). "Room temperature storage of mouse epididymal spermatozoa: exploration of factors affecting sperm survival." Theriogenology 61(7-8): 1455-1469.
WHO (2010). "WHO laboratory manual for the examination and processing of human semen."

* cited by examiner

*Primary Examiner* — Ralph J Gitomer
(74) *Attorney, Agent, or Firm* — Mark M. Friedman

(57) ABSTRACT

The present invention refers to field of assisted reproductive technologies, in particular to a sperm storage media, and describes mTOR enhancers, preferably the mTOR activator MHY 1485, as supplement for storage media, said supplemented media increasing sperm motility and viability during short-term room temperature storage, while sustaining the metabolic rates, without changing its fertilization potential (capacitation) and DNA integrity.

7 Claims, 3 Drawing Sheets

SPERM STORAGE MEDIA COMPRISING MHY 1485 FOR ENHANCING SPERM QUALITY AND FUNCTION

FIELD OF THE INVENTION

The present invention refers to field of assisted reproductive technologies, in particular to a sperm storage medium to increase sperm quality and function.

PRIOR ART

In the last decades, the number of individuals seeking for assisted reproduction techniques (ART) has been increasing (Elder and Dale 2010). Sperm quality is a very important factor in the in vitro fertilization (IVF) laboratory since male infertility accounts for up to 30% of the infertility cases and treatment options are mainly based on sperm-quality improvement techniques (WHO 2010). Concerning male reproductive biology, great efforts are being made to prolong viability of stored sperm, as it is a key factor for the success of ART (Jackson, Bormann et al. 2010). Cryopreservation and refrigeration of sperm have been highly debated, and it has been proposed that the maintenance of sperm at room/body temperature (RT) for short-term periods can be an effective alternative to avoid the rapid decline of sperm viability after storage in refrigerated environment (Sato and Ishikawa 2004). Several storage media intended to maintain spermatozoa survival at RT are commercially available. However, in most, sperm viability after storage in those media is still far from the ideal. Establishment of optimal composition for sperm storage is of extreme relevance, as these cells are highly dependent on the supply of exogenous substrates and, due to their high metabolic rates, produce elevated amounts of ROS (Sato and Ishikawa 2004). The possibility to use substances to improve sperm viability, morphology and metabolism would be a major step in the treatment of male fertility.

The mammalian target of rapamycin (mTOR) is a highly conserved multifunctional serine/threonine protein kinase that regulates several crucial cellular events. However, though it has been suggested that mTOR integrates and mediates signals throughout the male reproductive system, there is lack of evidence for its role in spermatogenesis (Oliveira, Cheng et al. 2017). Our first results were attained in the somatic testicular cells and showed that mTOR controls glucose consumption and redox balance in human Sertoli cells. Thus, it appears that mTOR plays a central role in the nutritional support of spermatogenesis (Jesus, Oliveira et al. 2016).

Also, Aparicio et al. (2016) showed that autophagy related proteins and upstream regulators are present and functional in human spermatozoa. Modification of mitochondrial proteins expression after autophagy activation/inhibition (using a high concentration mTOR inhibitor, Rapamycin) may be indicating that a specialized form of autophagy named mitophagy regulating sperm function such as motility and viability and may be cooperating with apoptosis. However, the fact that a commercial storage medium can be supplemented with the mTOR activator MHY 1485 in low concentration to increase sperm motility and viability during short-term room temperature storage, while sustaining the metabolic rates and without changing its fertilization potential (capacitation) and DNA integrity has never been disclosed before.

Improving the available sperm storage media in order to increase the sperm quality after storage is thus a longfelt need in the treatment of infertility using Assisted Reproduction Technologies.

Solved Technical Problems

As detailed below, the present invention is directed into the problem of storing sperm for assisted reproduction techniques, and proposes an alternative solution which provides increased sperm quality and function.

The present invention describes the mTOR activator MHY 1485 as supplement for storage media, said supplemented media increasing sperm motility and viability during short-term room temperature storage, while sustaining the metabolic rates, without changing its fertilization potential (capacitation) and DNA integrity.

The use of mTOR activators thus improves specific sperm quality parameters, while maintaining its integrity and quality during short-term RT storage. This discovery is of extreme relevance since has great impact in sperm storage at room/body temperature but also other applications where control of sperm physiology is pivotal. This invention improves the available sperm storage media and is extremely valuable in the treatment of infertility using Assisted Reproduction Technologies, and to increase sperm quality after storage at room/body temperature.

DESCRIPTION OF THE INVENTION

DETAILED DESCRIPTION OF THE INVENTION

Figure 1:
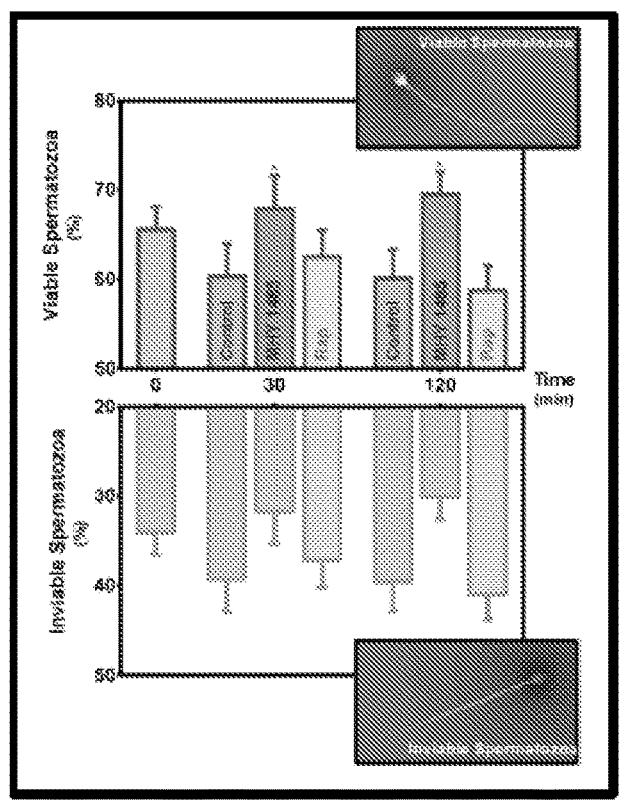
FIG. 1—Human spermatozoa viability after storage during 120 minutes at 37° C. Spermatozoa were stored in Sperm Preparation Medium (ORIGIO, Måløv, Denmark) not supplemented (Control) or supplemented with an mTOR activator (MHY 1485). Spermatozoa were also incubated with an mTOR inhibitor (Rapamycin; Rap) as a negative control. Viability was assessed by the eosin-nigrosin staining method. Results are presented as mean±standard error of the mean (n=12); Significant results (P<0.05) are indicated as *-vs. Control.

The present invention concerns a sperm quality and function enhancing composition characterized by comprising an activator of mTOR.

In a preferred embodiment, the mTOR activator is MHY 1485.

The present invention also concerns a sperm quality and function enhancing supplement for sperm storage media characterized by comprising an activator of mTOR.

In a preferred embodiment, the mTOR activator is MHY 1485.

In an more preferred embodiment, the supplement is suitable for room temperature or body temperature storage.

In another more preferred embodiment, the supplement is suitable for short term storage.

The invention also concerns a sperm quality and function enhancing storage media characterized by comprising an activator of mTOR.

In a preferred embodiment, the mTOR activator is MHY 1485. In a more preferred embodiment, the amount of MHY 1485 in the storage media is 2 µg/mL.

In an even more preferred embodiment, the storage media is suitable for room temperature or body temperature storage.

In another preferred embodiment, the storage media is suitable for short term storage.

The invention also concerns a method of enhancing sperm quality and function during storage characterized by depositing the sperm in storage media supplemented with an mTOR activator.

In a preferred embodiment, the mTOR activator is MHY 1485. In a more preferred embodiment, the amount of MHY 1485 added to the storage media is 2 µg/mL.

In a more preferred embodiment, the sperm is stored at room temperature or body temperature.

The invention also concerns a method of increasing the likelihood of fertilization by a sperm cell comprising storing sperm in a storage medium supplemented with an mTOR activator and further using the stored sperm in an assisted reproductive technology.

In a preferred embodiment, the storage medium is supplemented with MHY 1485.

In a more preferred embodiment, the amount of MHY 1485 added to the media is 2 µg/mL.

Example

We evaluated the use of an mTOR activator (MHY 1485) as an additive during sperm storage at 37° C. We added the mTOR activator (at a concentration of 2 µg/mL) to a commercial sperm storage medium (Sperm Preparation Medium®; Origio, Malay, Denmark) and stored the spermatozoa suspension (2 million spermatozoa per mL) in microtubes (at 37° C. in a 5% CO2 incubator) for up to 120 minutes, evaluating key parameters of quality and the degree of oxidative damages to those cells at regular intervals (0, 30 and 120 minutes). We assessed key sperm quality parameters, namely sperm viability and sperm motility, using standard methods, as described by the guidelines of the World Health Organization, with the supervision of a certified embryologist. We also evaluated the oxidative damages to sperm DNA (DNA fragmentation), proteins (protein carbonylation) and lipids (lipid peroxidation). Sperm DNA fragmentation was assessed using the Halosperm® kit (Halotech DNA SL, Madrid, Spain). Sperm protein carbonylation and lipid peroxidation were evaluated using specific antibodies (ABCAM®, Cambridge, USA) raised against 2,4-dinitrophenol groups and anti-4-hydroxynonenal groups (respectively). The metabolic alterations of spermatozoa were also evaluated by means of the proton magnetic resonance technique (1H-NMR), using a Varian 600 MHz spectrometer equipped with a 3 mm indirect detection probe with z-gradient (Varian, Palo Alto, USA). At the end of the storage, we evaluated the capacitation potential of the spermatozoa, by incubating the cells in a commercial medium (Lifeglobal®, Guilford, USA) and assessing the 3-nitrotyrosine levels using specific antibodies (ABCAM®, Cambridge, USA). An mTOR inhibitor (Rapamycin at a concentration of 0,1 µg/mL) was used as a negative control.

The storage of spermatozoa at 37° C. caused a decrease in its viability as soon as after 30 minutes. The supplementation of the commercial storage medium with the mTOR activator maintained the percentage of viable sperm at similar levels as those of time zero (FIG. 1).

Figure 2:
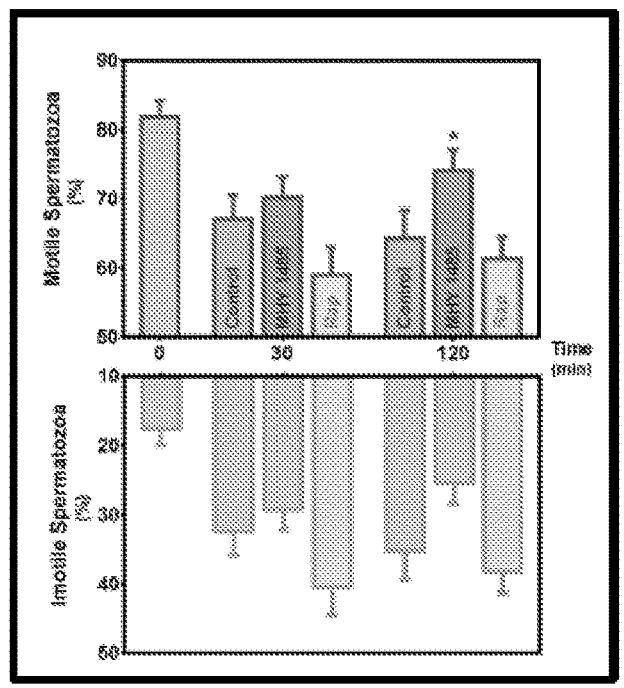
FIG. 2—Human spermatozoa motility after storage during 120 minutes at 37° C. Spermatozoa were stored in Sperm Preparation Medium (ORIGIO, Måløv, Denmark) not supplemented (Control) or supplemented with an mTOR activator (MHY 1485). Spermatozoa were also incubated with an mTOR inhibitor (Rapamycin; Rap) as a negative control. Results are presented as mean±standard error of the mean (n=12); Significant results (P<0.05) are indicated as *-vs. Control.
Figure 3:
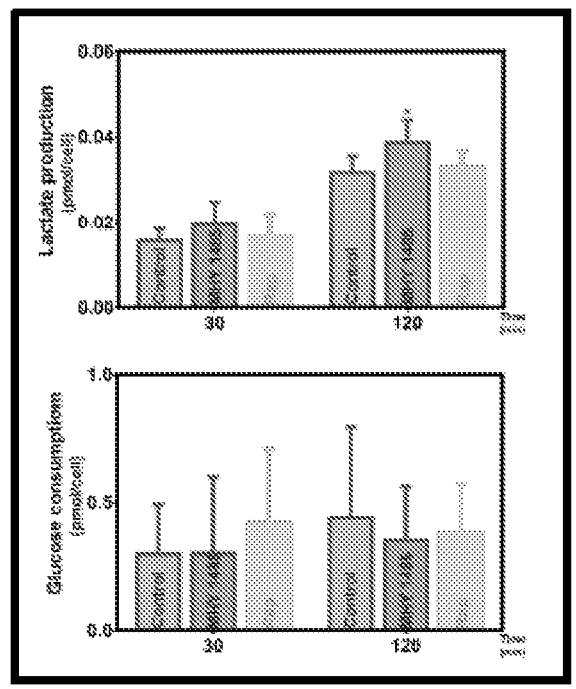
FIG. 3—Human spermatozoa metabolism during storage for 120 minutes at 37° C. Spermatozoa were stored in Sperm Preparation Medium (ORIGIO, Måløv, Denmark) not supplemented (Control) or supplemented with an mTOR activator (MHY 1485). Spermatozoa were also incubated with an mTOR inhibitor (Rapamycin; Rap) as a negative control. Sperm glucose consumption and lactate production were assessed by 1H nuclear magnetic resonance. Results are presented as mean±standard error of the mean (n=12); Significant results (P<0.05) are indicated as *-vs. Control.

Moreover, spermatozoa motility was progressively decreased during the storage, with the mTOR activator being capable to maintain sperm motile (FIG. 2) and to sustain its capacitation potential. When basic aspects of sperm metabolism were assessed, such us the consumption of hexoses and the production of lactate, no differences were observed after 30 minutes of storage (FIG. 3).

Figure 4:
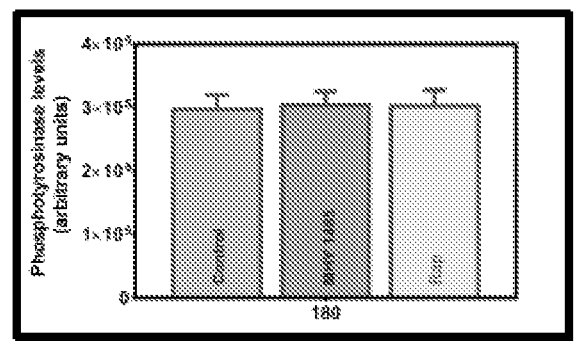
FIG. 4—Human spermatozoa capacitation after storage for 120 minutes at 37° C. Spermatozoa were stored in Sperm Preparation Medium (ORIGIO, Måløv, Denmark) not supplemented (Control) or supplemented with an mTOR activator (MHY 1485). Spermatozoa were also incubated with an mTOR inhibitor (Rapamycin; Rap) as a negative control. Sperm capacitation was assessed by evaluating sperm phosphotyrosine levels after 180 minutes incubation in Sperm Capacitation Medium (LifeGlobal Europe, Brussels, Belgium). Results are presented as mean±standard error of the mean (n=12); Significant results (P<0.05) are indicated as *-vs. Control.
Figure 5:
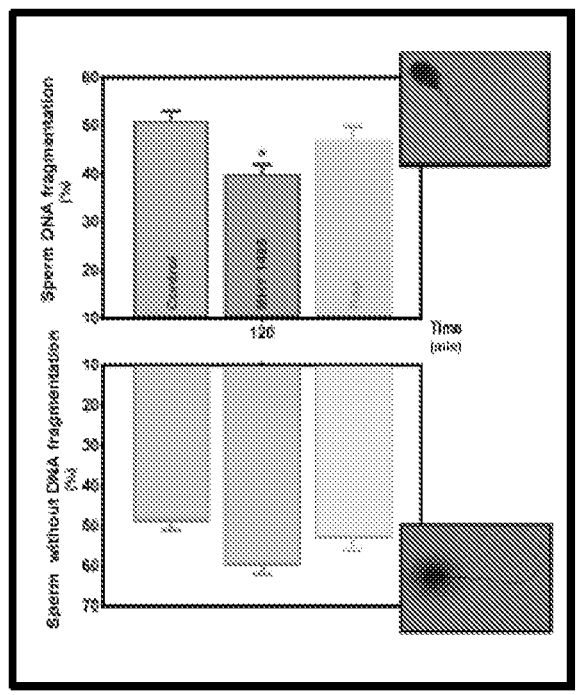
FIG. 5—Human spermatozoa DNA fragmentation after storage for 120 minutes at 37° C. Spermatozoa were stored in Sperm Preparation Medium (ORIGIO, Måløv, Denmark) not supplemented (Control) or supplemented with an mTOR activator (MHY 1485). Spermatozoa were also incubated with an mTOR inhibitor (Rapamycin; Rap) as a negative control. DNA fragmentation was assessed using a Halosperm G2 kit (HALOTECH, Madrid, Spain). Results are presented as mean±standard error of the mean (n=12); Significant results (P<0.05) are indicated as *-vs. Control.
Figure 6:
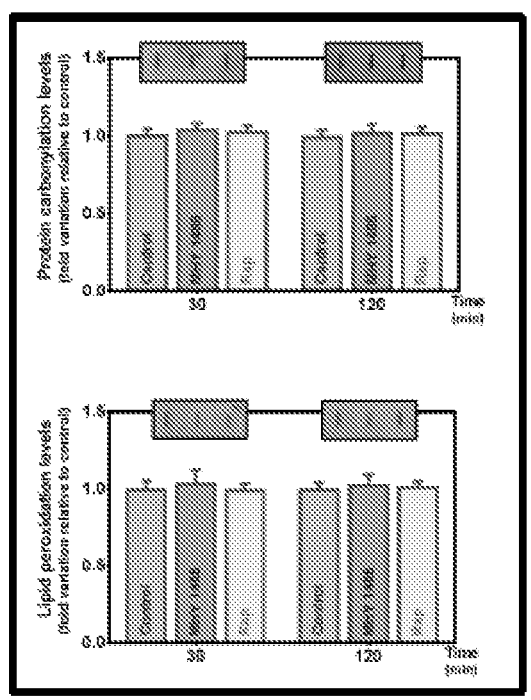
FIG. 6—Human spermatozoa oxidative damage to proteins (carbonylation) and lipids (peroxidation) after storage for 120 minutes at 37° C. Spermatozoa were stored in Sperm Preparation Medium (ORIGIO, Måløv, Denmark) not supplemented (Control) or supplemented with an mTOR activator (MHY 1485). Spermatozoa were also incubated with an mTOR inhibitor (Rapamycin; Rap) as a negative control. Protein carbonylation was assessed by immunobloting a specific @DNP antibody (SigmaAldrich, St. Louis, Mo., USA). Lipid peroxidation was assessed by immunobloting a specific @HNE antibody (Merck Millipore, Temecula, USA). Results are presented as mean±standard error of the mean (n=12); Significant results (P<0.05) are indicated as *-vs. Control.

These results were even more promising when considering the 120 minutes of sperm storage, since mTOR activator was capable to preserve sperm viability and its capacitation potential (FIG. 4), sustaining a higher motility. In these spermatozoa stored in the presence of the mTOR activator during 120 minutes, glucose consumption was maintained, while lactate production was increased. Worthy of note is that sperm oxidative damages were not increased, with DNA remaining fully intact after treatment (FIG. 5). Sperm protein oxidative damage (protein carbonylation) as well as lipid oxidative damage (lipid peroxidation) were also not increased in the samples stored in the presence of the mTOR activator during 120 minutes (FIG. 6).

REFERENCES

I. M. Aparicio, J. Espino, I. Bejarano, A. Gallardo-Soler, M. L. Campo and G. M. Salido (2016). "Autophagy-related proteins are functionally active in human spermatozoa and may be involved in the regulation of cell survival and motility." Scientific Reports 6: 33647.

J. A. Pariente2, F. J. Peña4 & J. A. Tapial Elder, K. and B. Dale (2010). In-vitro fertilization, Cambridge University Press.

Jackson, R. E., C. L. Bormann, P. A. Hassun, A. M. Rocha, E. L. Motta, P. C. Serafini and G. D. Smith (2010). "Effects of semen storage and separation techniques on sperm DNA fragmentation." Fertility and sterility 94(7): 2626-2630.

Jesus, T. T., P. F. Oliveira, J. Silva, A. Barros, R. Ferreira, M. Sousa, C. Y. Cheng, B. M. Silva and M. G. Alves (2016). "Mammalian target of rapamycin controls glucose consumption and redox balance in human Sertoli cells." Fertil. Steril. 105(3): 825-833.e823.

Oliveira, P. F., C. Cheng and M. G. Alves (2017). "Emerging Role for Mammalian Target of Rapamycin in Male Fertility." Trends in Endocrinology & Metabolism: DOI: 10.1016/j.tem.2016.1012.1004.

Sato, M. and A. Ishikawa (2004). "Room temperature storage of mouse epididymal spermatozoa: exploration of factors affecting sperm survival." Theriogenology 61(7-8): 1455-1469.

WHO (2010). "WHO laboratory manual for the examination and processing of human semen."

We claim:

1. A sperm storage media for enhancing sperm quality and function, wherein the sperm storage media comprises a supplement containing MHY 1485.

2. The sperm storage media for enhancing sperm quality and function according to claim 1, wherein the supplement is suitable for room temperature or body temperature storage.

3. The sperm storage media for enhancing sperm quality and function according to claim 1, wherein the supplement is suitable for short-term storage.

4. A sperm storage media for enhancing sperm quality and function comprising MHY 1485.

5. The sperm storage media for enhancing sperm quality and function according to claim 4, wherein the concentration of MHY 1485 is 2 µg/mL.

6. The sperm storage media for enhancing sperm quality and function according to claim 4, wherein the storage media is suitable for room temperature or body temperature storage.

7. The sperm storage media for enhancing sperm quality and function according to claim 4, wherein the storage media is suitable for short-term storage.

* * * * *